United States Patent
Yin et al.

(10) Patent No.: US 7,532,705 B2
(45) Date of Patent: May 12, 2009

(54) SYSTEMS AND METHODS FOR LOCALIZING A TARGET FOR RADIOTHERAPY BASED ON DIGITAL TOMOSYNTHESIS

(75) Inventors: Fang-Fang Yin, Chapel Hill, NC (US); Devon J. Godfrey, Hillsborough, NC (US); Mark Oldham, Durham, NC (US); James T. Dobbins, III, Durham, NC (US)

(73) Assignee: Duke University, Durham, NC (US)

( * ) Notice: Subject to any disclaimer, the term of this patent is extended or adjusted under 35 U.S.C. 154(b) by 187 days.

(21) Appl. No.: 11/786,075

(22) Filed: Apr. 10, 2007

(65) Prior Publication Data

US 2007/0291895 A1    Dec. 20, 2007

Related U.S. Application Data

(60) Provisional application No. 60/790,685, filed on Apr. 10, 2006.

(51) Int. Cl.
*A61N 5/10* (2006.01)
(52) U.S. Cl. .................. 378/65; 378/22; 382/294
(58) Field of Classification Search .................. 378/22, 378/65; 382/131, 294
See application file for complete search history.

(56) References Cited

U.S. PATENT DOCUMENTS

| 4,868,857 | A | 9/1989 | Dobbins, III |
| 4,903,204 | A | 2/1990 | Dobbins, III |
| 6,970,531 | B2 | 11/2005 | Eberhard et al. |
| 2005/0105679 | A1 | 5/2005 | Wu et al. |
| 2005/0180544 | A1 | 8/2005 | Sauer et al. |
| 2005/0251010 | A1* | 11/2005 | Mistretta et al. ............ 600/407 |
| 2005/0259891 | A1* | 11/2005 | Sendai ...................... 382/294 |
| 2007/0025509 | A1* | 2/2007 | Pang et al. .................... 378/65 |

OTHER PUBLICATIONS

Baydush et al., Initial application of digital tomosynthesis with on-board imaging in radiation oncology, Feb. 13, 2005, SPIE Medical Imaging 2005: Physics in medical Imaging, vol. 5745, pp. 1300-1305.*

* cited by examiner

*Primary Examiner*—Edward J Glick
*Assistant Examiner*—John M Corbett
(74) *Attorney, Agent, or Firm*—Jenkins, Wilson, Taylor & Hunt, P.A.

(57) ABSTRACT

Systems and methods for localizing a target for radiotherapy based on digital tomosynthesis are provided. According to one method, DTS verification image data of a target located within or on a patient is generated. The DTS verification image data is compared with DTS reference image data of the target. Radiotherapy positioning information is determined based on the comparison of the DTS verification and reference image data.

44 Claims, 9 Drawing Sheets

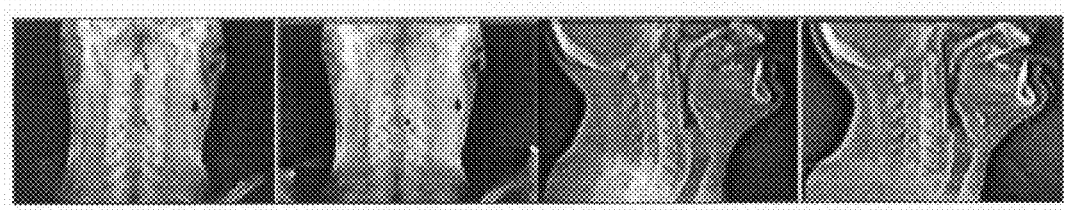
FIG. 6A RDTS    FIG. 6B DTS    FIG. 6C RDTS    FIG. 6D DTS
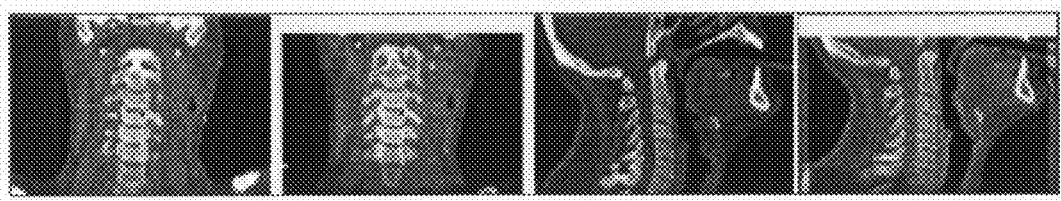
FIG. 7A CT    FIG. 7B CBCT    FIG. 7C CT    FIG. 7D CBCT
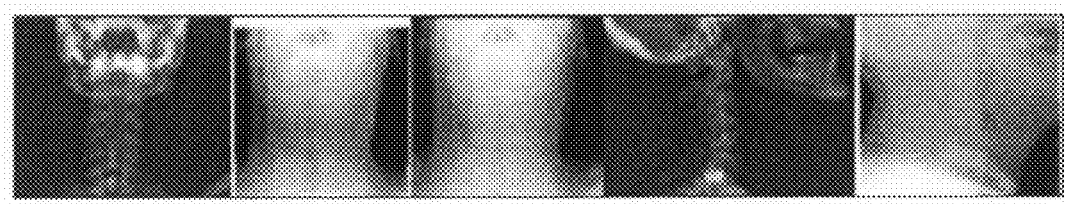
FIG. 8A DRR    FIG. 8B MVrad    FIG. 8C kVrad    FIG. 8D DRR    FIG. 8E MVrad
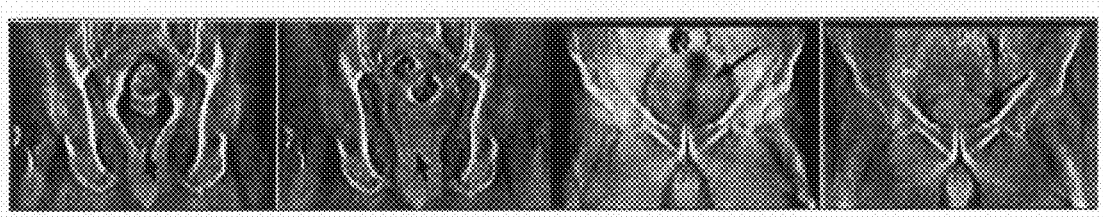
FIG. 9A RDTS    FIG. 9B DTS    FIG. 9C RDTS    FIG. 9D DTS
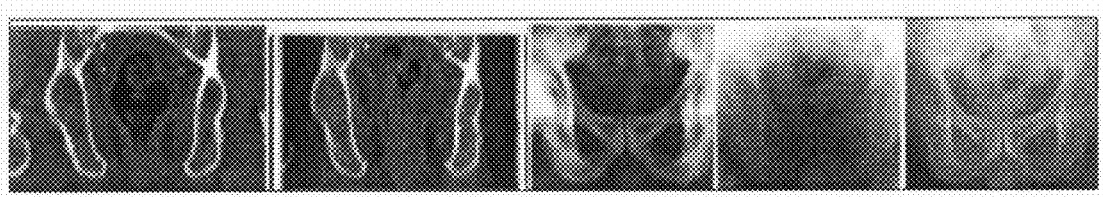
FIG. 10A CT    FIG. 10B CBCT    FIG. 11A DRR    FIG. 11B MVrad    FIG. 11C RVrad

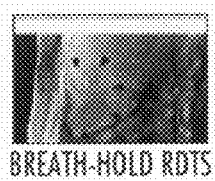
BREATH-HOLD RDTS
FIG. 12A
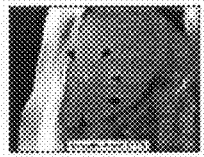
BREATH-HOLD DTS
FIG. 12B
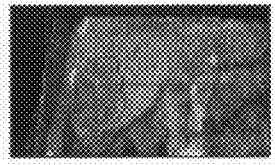
FIG. 13A
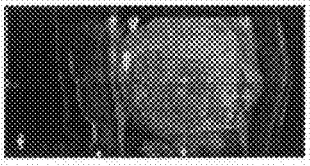
FIG. 13B
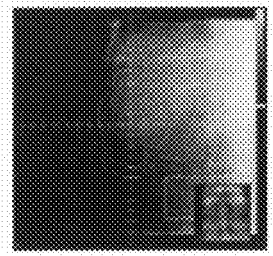
FIG. 14A
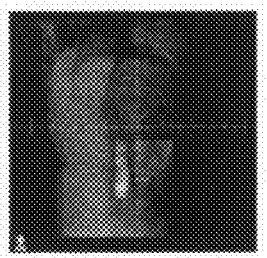
FIG. 14B
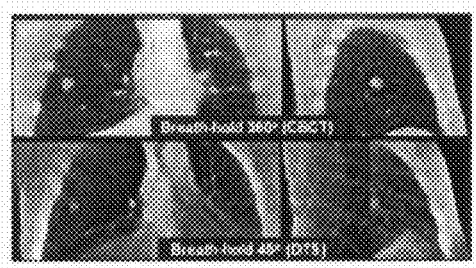
FIG. 15A
FIG. 15B
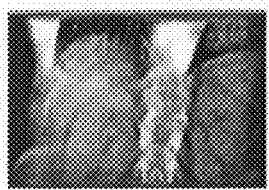
BREATH-HOLD RDTS
FIG. 16A
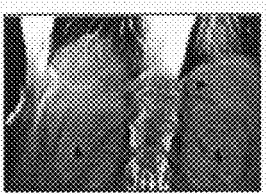
BREATH-HOLD DTS
FIG. 16B
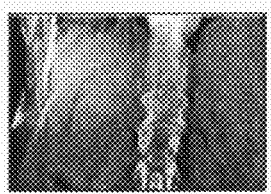
FREE-BREATHING DTS
FIG. 17
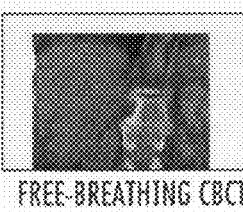
FREE-BREATHING CBCT
FIG. 18
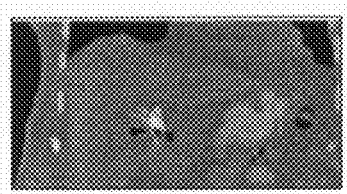
BREATH-HOLD REFERENCE DTS
FIG. 19A
BREATH-HOLD ON-BOARD DTS
FIG. 19B
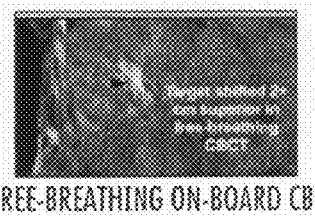
BREATH-HOLD PLANNING CT
FIG. 20A
FREE-BREATHING ON-BOARD CBCT
FIG. 20B

SYSTEMS AND METHODS FOR LOCALIZING A TARGET FOR RADIOTHERAPY BASED ON DIGITAL TOMOSYNTHESIS

RELATED APPLICATIONS

The presently disclosed subject matter claims the benefit of U.S. Provisional Patent Application Ser. No. 60/790,685, filed Apr. 10, 2006; the disclosure of which is incorporated herein by reference in its entirety.

TECHNICAL FIELD

The subject matter disclosed herein relates to target localization and patient positioning for radiotherapy. More particularly, the subject matter disclosed herein relates to systems and methods for localizing a target for radiotherapy based on digital tomosynthesis (DTS).

BACKGROUND

Three-dimensional (3-D) conformal radiation therapy and intensity-modulated radiation therapy (IMRT) are used to deliver radiation precisely to a target. These advanced delivery techniques can potentially reduce the amount of normal tissue receiving high dose irradiation and thus allow for the prescription of higher doses to tumors to potentially improve the probability of local-regional disease control. However, the amount of normal tissue reduction is dependent on the amount of the treatment margin added when expanding from a clinical target volume (CTV) to a planning target volume (PTV), as required to accommodate setup variations and organ motion. This margin could potentially be reduced if the treatment volume could routinely be identified and localized with high accuracy prior to treatment delivery. The most effective approach to minimize all potential localization deviations is the use of real-time (or on-board) procedures when the patient is in the treatment position immediately prior to radiation delivery.

An array of image-guided technologies has been developed to improve localization accuracy in the treatment room. Exemplary image-guided technologies include optical, ultrasound, and radiographic imaging. Among these technologies, radiographic imaging is most frequently employed for on-board target localization.

Effective delivery of therapeutic radiation depends upon accurate localization of the therapy target at the time of treatment. In general, therapy plans are devised using the image volume from a "planning" computed tomography (CT) image set, acquired weeks in advance of the actual treatment. During setup for actual radiation therapy treatment, an attempt is made to match a patient's positioning on the treatment couch with their previous positioning during the planning CT acquisition. Historically, daily target localization was performed using external landmarks (e.g., skin markers), lasers mounted in the treatment room, and film images acquired using short exposures with the treatment beam.

Current on-board radiographic imaging techniques includes two-dimensional (2-D) (or projection) radiographic imaging using either kilovoltage (kV) or megavoltage (MV) sources, 2-D fluoroscopic kV imaging, and 3-D tomographic imaging using on-board cone-beam CT (QBCT) and CT-on-rails systems. 2-D radiographic imaging is a simple and an efficient imaging technique and delivers low radiation dose. However, verification of the target position is based primarily on visible bony structures or implanted fiducials. Although kV radiographs exhibit better tissue contrast than MV portal images, both are projection images and are sub-optimal since multi-layered 3D anatomy is projected onto a single image plane.

On-board CBCT renders 3-D anatomy and provides visualization of soft-tissue targets. The ability to match 3-D soft tissue between planning CT (or reference CT) images and on-board CBCT (or verification CBCT) images allows medical practitioners to verify true target positioning. However, CBCT application in radiation therapy for on-board targeting has several drawbacks. In one example, CBCT acquisition typically requires about 60 seconds with a full gantry rotation, which covers about 15 breathing cycles. Thus, single breath-hold CBCT is impractical. Therefore, when organs move during respiration, CBCT can only generate a blurred composite organ volume rather than a true organ volume. Although some 4-D CBCT image acquisition techniques are being investigated, they either require long imaging time (such as segmented breath-hold acquisitions), deliver poor image quality (e.g., re-binning of projection data from a gated image acquisition), or excessive dose (e.g., respiratory re-sorting technique).

In another example of a drawback of CBCT, CBCT requires full rotational clearance of the gantry with respect to the position of the patient and couch. This is potentially problematic for patients with tumors at peripheral locations (e.g., breast) or for those patient requiring substantial immobilization and supportive devices. Although smaller rotation angles (180 degrees plus a fan angle) may be reasonable for CBCT reconstruction, it still requires clearance of 360 degrees for gantry rotation.

In yet another example of a drawback of CBCT, CBCT radiation dose can range from 2 to 9 cGy for optimal image quality. Daily or weekly imaging will result in higher cumulative doses. This dose is generally applied to a much larger volume than the intended treatment volume. Reducing image dose is critical for those patients at high risk of developing second malignancies.

The above-described drawbacks can adversely affect the efficiency and efficacy of CBCT for image-guided radiation therapy (IGRT). In general, the acquisition time and clearance limitations of CBCT for on-board imaging in radiation oncology are not due to CBCT itself, but are principally due to the mechanical limitations of on-board CBCT mounted on the heavy gantry of a linear accelerator. In radiation oncology, the treatment gantry in a linear accelerator is not allowed to rotate faster than one revolution per minute (7 degrees per second limited by International Electrotechnical Commission (IEC) standards and 6 degrees per second by manufacturer specifications for safety reasons). Therefore, it is unlikely that the imaging time for a conventional treatment unit with CBCT capability will be improved upon soon. Such improvements would require regulatory changes based on safety considerations. As a result of these limitations, there exists a need for improved on-board imaging techniques that can efficiently provide 3-D anatomical information with minimal imaging dose and mechanical clearance requirements.

Digital tomosynthesis is a technique for reconstructing a stack of 3-D slices from 2-D cone-beam x-ray projection data acquired with limited source angulation (~40°) or scan angle. By resolving overlying anatomy into slices, DTS can enhance the visibility of anatomy compared with 2-D kV or MV radiographic imaging. Furthermore, DTS requires less radiation exposure (less than 20% of CBCT dose) and unobstructed gantry rotation clearance, and can be implemented with a shorter scan time (at least a factor of 9) than CBCT. As a result of the quick nature of DTS acquisition, organ motion can likely be better managed with DTS technology. These advantages make DTS attractive for daily patient positioning verification and 3-D target localization, especially for those who may be at risk of second malignancies, such as young and pediatric patients. Because DTS uses only a small subset of CBCT projections, it will always be faster, and will have fewer clearance limitations than CBCT. Thus, the improvements available for CBCT will also likely be applicable to DTS. There will always be an incremental benefit of DTS over CBCT in terms of acquisition time and clearance. DTS will also require lower dose than CBCT for comparable image quality because the total dose is subdivided over fewer projections with DTS than CBCT, thereby mitigating the effect of additive detector noise.

Accordingly, in light of these difficulties associated with conventional radiation therapy technologies, there exists a need for improved systems and methods for radiotherapy based on DTS.

SUMMARY

The subject matter described herein includes systems and methods for positioning a patient for radiotherapy based on digital tomosynthesis. According to one aspect, a method includes generating DTS verification image data of a target located within or on a patient. The DTS verification image data can be compared with DTS reference image data of the target. Radiotherapy positioning information can be determined based on the comparison of the DTS verification and reference image data.

According to another aspect, a system for positioning a patient for radiotherapy based on digital tomosynthesis includes a DTS verification image data generator configured to generate DTS verification image data of a target located within or on a patient. Further, the system can include a DTS verification and reference image data comparator configured to compare the DTS verification image data with DTS reference image data of the target. A radiotherapy positioning module can determine radiotherapy positioning information based on the comparison of the DTS verification and reference image data.

BRIEF DESCRIPTION OF THE DRAWINGS

Preferred embodiments of the subject matter described herein will now be described with reference to the accompanying drawings, of which:

FIGS. 6A-6D are DTS reference and verification images of a head-and-neck subject in coronal and sagittal views acquired using systems and methods in accordance with the subject matter described herein;

FIGS. 7A-7D are planning CT and CBCT images of the head-and-neck subject shown in FIGS. 6A-6D;

FIGS. 8A-8E are planning DRR, MV, and kV radiographs of the head-and-neck subject shown in FIGS. 6A-6D;

FIGS. 9A-9D are DTS reference and verification images of a prostate subject in the coronal view acquired using systems and methods in accordance with the subject matter described herein;

FIGS. 10A and 10B are planning CT and CBCT images, respectively, of the prostate subject shown in FIGS. 9A-9D in the coronal view;

FIGS. 11A-11C are planning DRR, MV, and kV radiographs, respectively, of the prostate subject shown in FIGS. 9A-9D in the coronal view;

FIGS. 12A and 12B are DTS reference and verification images, respectively, of a breath-hold liver subject acquired using systems and methods in accordance with the subject matter described herein;

FIGS. 13A and 13B are planning CT images of the subject shown in FIGS. 12A and 12B in coronal and sagittal views, respectively;

FIGS. 14A and 14B are orthogonal kV radiographs of the subject shown in FIGS. 12A and 12B;

FIGS. 15A and 15B are CBCT and DTS images, respectively, of the thoracic subject in coronal and sagittal views;

FIGS. 16A and 16B are breath-hold reference and verification DTS images, respectively, of the liver subject in the coronal view;

FIG. 17 is a free-breathing DTS image of the same liver subject in the coronal view;

FIG. 18 is a free-breathing CBCT image of the same liver subject in the coronal view;

FIGS. 19A and 19B are breath-hold reference and verification DTS images, respectively, of a liver subject acquired in accordance with the subject matter described herein;

FIGS. 20A and 20B are breath-hold planning CT and free-breathing on-board CBCT images, respectively, of the same liver subject shown in FIGS. 19A and 19B;

DETAILED DESCRIPTION

The subject matter described herein includes systems and methods for positioning a patient for radiotherapy based on DTS. According to one aspect, a method according to an embodiment of the subject matter described herein can include generating DTS verification image data of a target located within or on a patient. The DTS verification image data can be compared with the DTS reference image data of the target. Radiotherapy positioning information can be determined based on the comparison of the DTS verification and reference image data. The target may be a radiation target or reference target employed for radiation treatment target localization.

As used herein, "reference image data" can be any suitable image data of a target located within or on a patient and acquired during a medical therapy planning stage and/or during medical treatment of the patient. The reference image data can be subsequently used for enabling target localization for a medical treatment procedure, such as radiotherapy. For example, the reference image data can be compared to verification image data of the same target for determining patient treatment positioning information. Exemplary types of reference image data include CT image data, CBCT image data, and DTS image data.

As used herein, "verification image data" can be any suitable image data of a target located within or on a patient and acquired for positioning the patient for treatment. The verification image data can be acquired immediately prior to, or during, or after treatment of the patient. For example, the verification image data can be acquired while the patient is on a treatment couch for radiotherapy. Target localization can be performed by comparing the location of the same target in reference image data and verification image data. Exemplary types of reference image data include 2-D radiographic images, and CT image data, CBCT image data, and DTS image data.

Figure 1A:
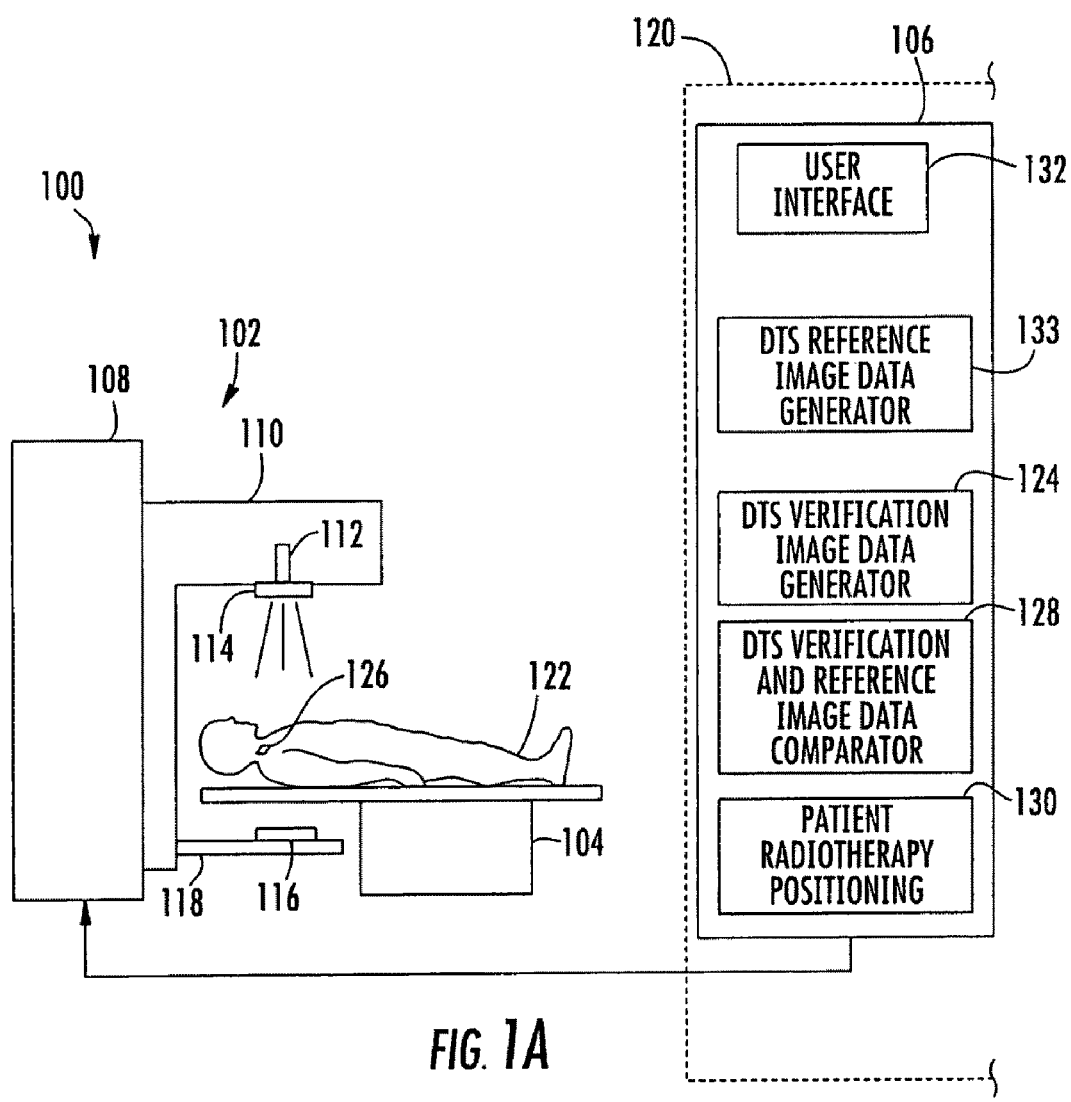
FIG. 1A is a block diagram of a system for positioning a patient for radiotherapy based on DTS according to an embodiment of the subject matter described herein.

FIG. 1A is a block diagram of a system 100 for positioning a patient for radiotherapy based on DTS according to an embodiment of the subject matter described herein. Referring to FIG. 1A, system 100 includes an OBI, or equivalent device which can generate digital radiographs using either kV or MV source, 102, a treatment bed (or treatment couch) 104, and a treatment unit 106. In one example, OBI 102 is a VARIAN 2100EX linear accelerator (available from Varian Medical Systems, Inc. of Palo Alto, Calif.). OBI 102 includes a kV x-ray source, a flat-panel detector mounted to the accelerator gantry, and a base 108, which includes a control unit for controlling OBI 102, and a gantry 110. Gantry 110 includes treatment MV source, an x-ray kilo volt (kV) imaging source 112, a beam-shielding device (not shown) with a treatment head 114, and a kV imaging panel, 116, and an electronic portal imaging device 118.

Gantry 110 can be swiveled about a horizontal axis during the course of radiotherapy or radiation treatment. Treatment head 114 is fixed to gantry 110 for movement therewith. Imaging source 112 can generate high-powered radiation such as electron, photon, or any other suitable detectable radiation. The movement of gantry 110 and distribution of radiation from imaging source 112 can be controlled by the control unit in response to commands issued by treatment unit 106. Treatment unit 106 may be located either in a room separate from where OBI 102 is located or in a shielded area 120 of a room where OBI 102 is located.

Electronic portal imaging device 118 can be mounted to gantry 110. Portal images can be obtained at any gantry angle and during rotation of gantry 110. Portal imaging device 118 can include imaging panel 116, which may be an active matrix flat panel (e.g., direct-detection detectors and indirect-detection amorphous silicon detectors) detector implemented as one or more arrays of photo-sensors. Panel 116 can measure the radiation exiting a patient 122. The amount of radiation exiting patient 122 can be used to gather the patient's exit dose information.

Images of patient 122 and target 126 can be obtained with OBI 102. The movement of gantry 110 causes imaging source 112 and panel 116 to rotate in tandem about a gantry isocenter during which image data can be obtained. In one example, resolution can be represented by the point spread function (PSF). In another example, resolution can be represented by the modulation transfer function (MTF). When the resolution is stationary throughout the image volume, these two resolution measures are essentially interchangeable since the MTF is the normalized modulus of the Fourier transform of the PSF. The PSF or MTF can also be used to characterize a DTS "slice profile," which describes how information throughout an imaged target contributes to a particular image slice.

Treatment unit 106 can include a central processing unit (CPU) and memory containing a computer program suitable for implementing the subject matter described herein. In particular, for example, the computer program can include instructions for operating components of system 100 to present patient radiotherapy positioning information to a medical practitioner for positioning a patient for radiotherapy. In particular, treatment unit 106 can include a DTS verification image data generator 124 configured to generate DTS verification image data of a target 126 located within or on patient 122. A DTS verification and reference image data comparator 128 can be configured to compare the DTS verification image data with DTS reference image data of target 126. A radiotherapy positioning module 130 can be configured to determine radiotherapy positioning information for patient 122 based on the comparison of the DTS verification and reference image data. Generator 124, comparator 128, and positioning module 130 can comprise hardware, software, firmware, or combinations thereof.

Treatment unit 106 can also include a user interface 132 suitable for interfacing with an operator, such as a medical practitioner. User interface 132 can comprise a keyboard, a mouse, and/or any other suitable devices with which an operator can input commands or data into unit 106. Further, user interface 132 can include one or more displays and/or any other suitable devices operable to present data to an operator.

In one embodiment, DTS localization includes generating DTS reference image data of a target located within or on a patient based on planning CT data of the target. Further, DTS localization includes generating DTS verification image data of the target prior to the treatment of the patient. The DTS reference and verification image data can be compared for determining patient set-up error. The image data can be used for registration of actual radiation delivery with a planned course of therapy.

In one embodiment, system 100 can be used for determining patient radiotherapy positioning information based on DTS verification and reference image data. In particular, DTS reference image data can be reconstructed from simulated cone-beam projections through a planning CT image volume. System 100 can be operated for reconstructing DTS reference images of a target, such as target 126 of patient 122, from simulated cone-beam projections through a planning CT image volume of the target. DTS reference images can also be generated using a conventional simulator as well as using a C-arm mobile imaging device.

DTS verification images can be generated from a small number of cone-beam projections acquired while patient 122 is positioned on treatment bed 104. For example, imaging source 112 and imaging device 118 can be controlled by generator 124 for generating cone-beam projections of target 126. The projections can be obtained at different angles by rotating gantry 110. Target localization can be performed by comparing landmarks (e.g., bony, soft-tissue anatomy, implanted targets, and/or skin contours, etc.) in the DTS reference and verification image data.

DTS reference image data of a target can be generated or acquired using any of a variety of suitable techniques. For example, DTS reference image data of a target may be generated based on CBCT image data of the target. The DTS reference image data of the target may be generated directly based on the CBCT image data. For example, the DTS reference image data may be generated directly from the CBCT image data without converting a set of CT images that are then reprojected.

In another example, DTS reference image data of a target can be generated based on simulator projection image data of the target. In this example, the DTS reference image data of the target can be generated using an x-ray tube and a flat panel detector or an image intensifier. DTS reference image data generator 133 can be configured to generate the DTS reference image data using either of these exemplary techniques.

In another example, DTS reference image data of a target can be generated based on a mobile c-arm x-ray unit projection image data of the target. In this example, the DTS reference image data of the target can be generated using an x-ray tube and a flat panel detector or an image intensifier. DTS reference image data generator 133 can be configured to generate the DTS reference image data using either of these exemplary techniques.

Figure 1B:
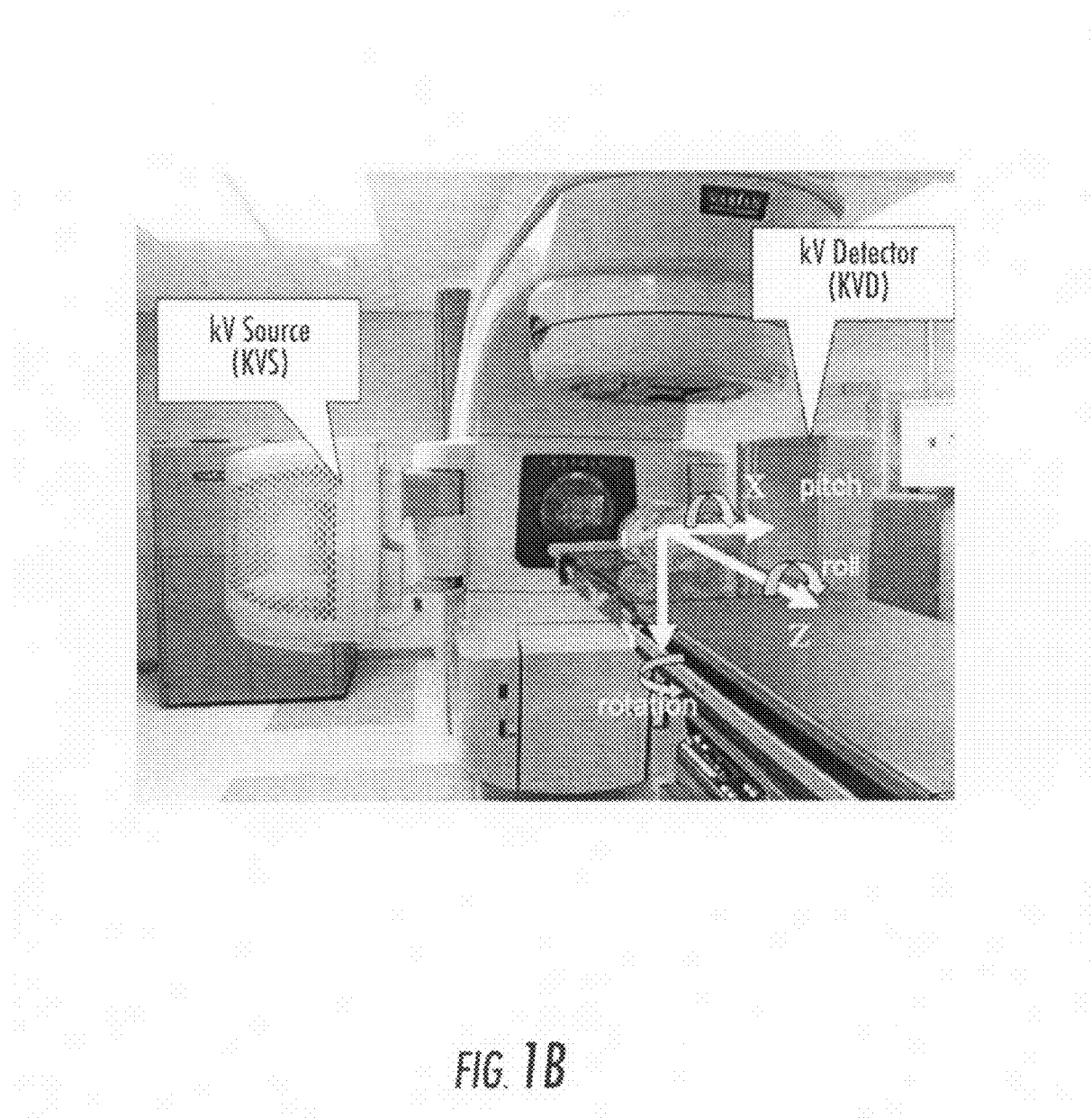
FIG. 1B is an image of an on-board imager (OBI) and treatment system.

FIG. 1B is an image of an OBI and treatment system. Referring to FIG. 1B, the system include two sources: an MV source and a kV source. Images can be acquired using the kV source. Treatment can be provided using the MV source. The kV source can be used to generate CBCT and DTS projection images. Further, the kV source can be used to generate 2-D radiographic images and fluoroscopic images. The MV source can be used as an x-ray source for acquiring radiographic images, performing fluoroscopic imaging, and acquiring CBCT and DTS projection images. Therefore, the system includes two sources and two detectors. However, the sources and detectors have different electronic gain factors and some configuration differences. X, Y, and Z designate the rotational positioning of an object for radiotherapy with respect to the treatment source based on radiotherapy position information determined or generated in accordance with the subject matter described herein.

Figure 2:
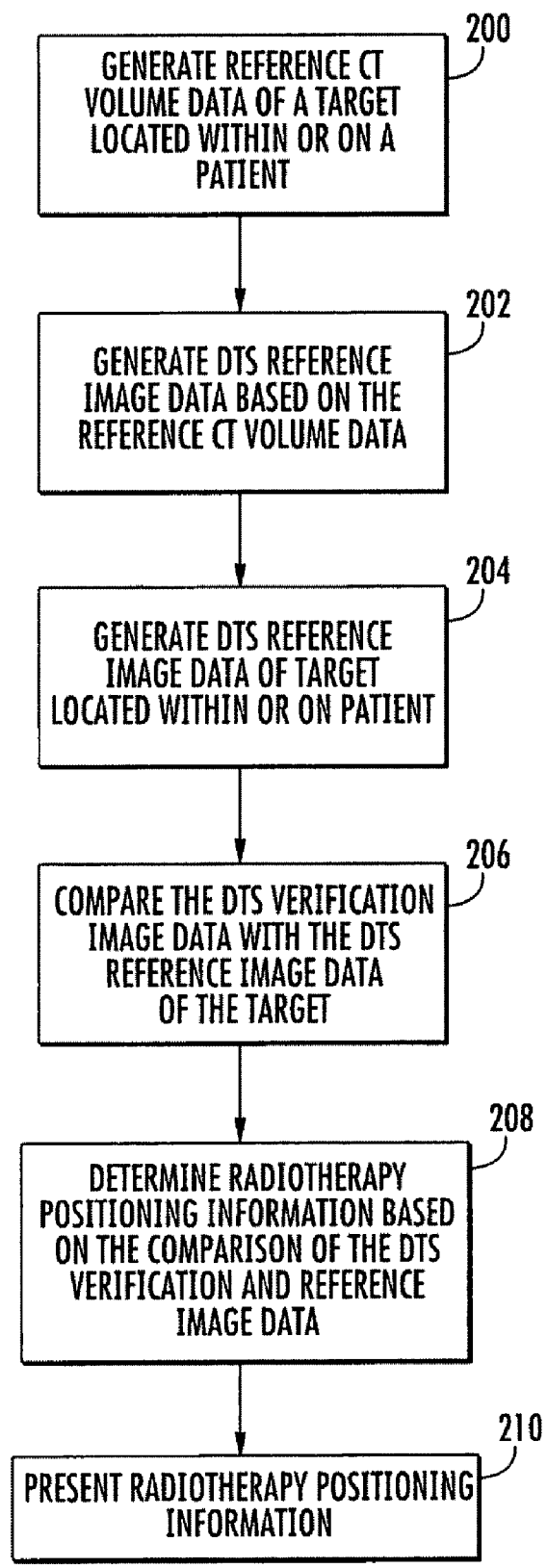
FIG. 2 is a flow chart of an exemplary process for positioning the patient shown in FIG. 1A for radiotherapy based on DTS according to an embodiment of the subject matter described herein.

FIG. 2 is a flow chart illustrating an exemplary process for positioning patient 122 shown in FIG. 1A for radiotherapy based on DTS according to an embodiment of the subject matter described herein. Referring to FIGS. 1 and 2, reference CT volume data of target 126 located within or on patient 122 is generated (block 200). In one example, the CT reference volume data can be acquired from patient 122 for planning radiotherapy of target 126, which may be a tumor or other target. Alternatively, target 126 may be a "marker" for use in targeting another target within patient 122 for radiotherapy. The reference CT image volume data can include CT slices stacked together to form a 3-D volume of patient 126. The CT slices can be obtained by system 100 and stored in memory of unit 106.

In block 202, DTS reference image data is generated based on the reference CT image volume data. For example, a DTS reference image generator 133 can be configured for generating DTS reference image data based on the reference CT image volume data of target 126. To generate a reference set for DTS registration, CT image volume data can be used to simulate reference DTS slices (RDTS). Generator 133 can be configured to compute simulated cone-beam projections through the CT image volume data by integrating attenuation values along ray-paths which extend from a predetermined (or presumed) location of an x-ray source to a predetermined (or presumed) location of an x-ray detector pixel. Generator 133 can select the predetermined x-ray source and detector locations to match actual source and detector pixel locations that are used when verification cone-beam projection data is acquired before radiotherapy.

Figure 3:
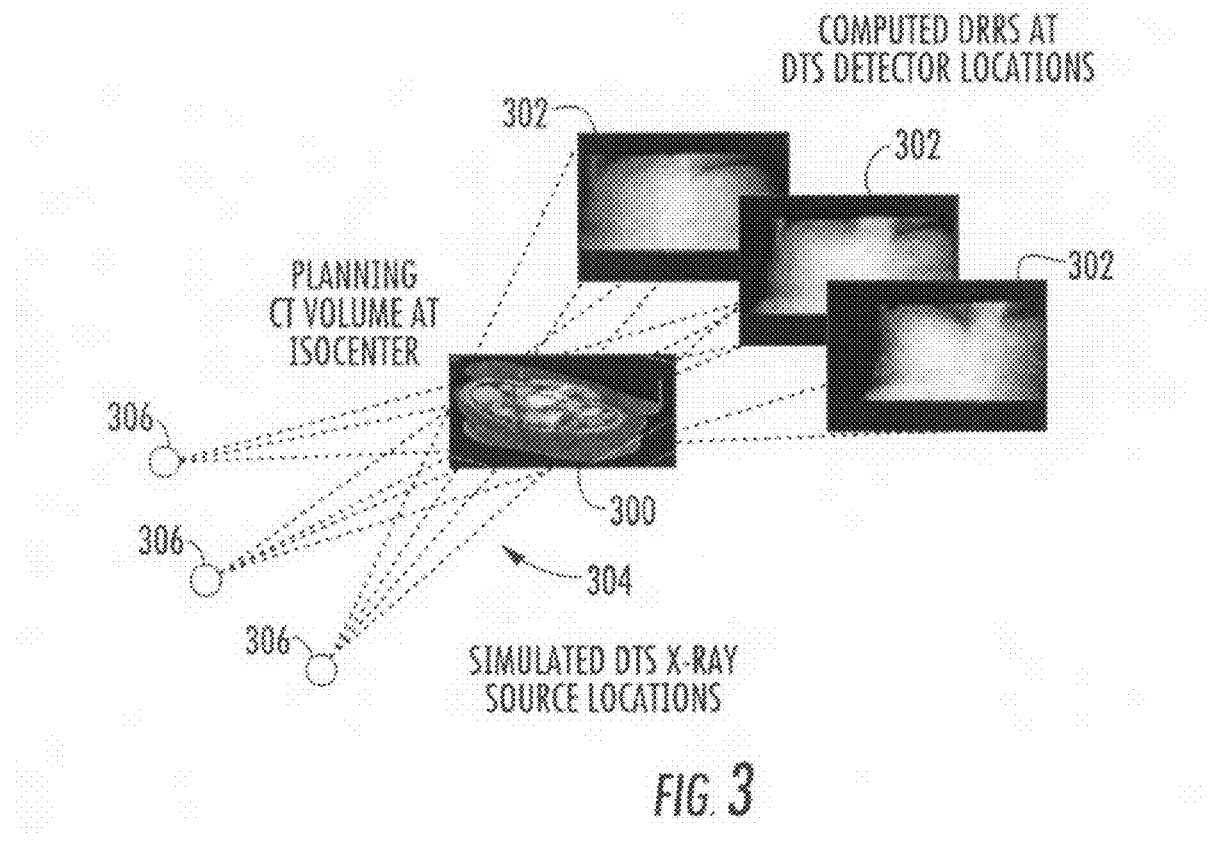
FIG. 3 is an image projection diagram of forward projection of a planning CT volume image at isocenter to generate multiple cone-beam digitally-reconstructed radiograph (DRR) images.

RDTS slices can be reconstructed from simulated cone-beam projections. The reconstructed RDTS slices can exactly match that of DTS verification images that are subsequently acquired, as described in further detail below. For registration purposes, reference DTS slices with any rigid-body shift or rotation can be similarly simulated. FIG. 3 is an image projection diagram illustrating forward projection of a planning CT volume image 300 at isocenter to generate multiple cone-beam DRR images 302. Referring to FIG. 3, the data of planning CT volume image 300 is used to simulate DRR images 302 by computing cone-beam projections through CT volume image 300 by integrating attenuation values along ray-paths, generally designated 304, which extend from a presumed location of x-ray sources 306 to a presumed location of an x-ray detector pixel. Reconstruction of DTS reference slices can be performed using the Feldkamp DTS algorithm as set forth with respect to the Feldkamp equation described hereinbelow.

Reference DTS plans can be reconstructed through the CT image volume from the simulated projection images using any suitable technique. In one example, a modified back-projection algorithm may be used for DTS reconstruction. Other exemplary DTS reconstruction algorithms include filtered backprojection, matrix inversion tomosynthesis (MITS), maximum likelihood expectation maximization (MLEM), and tuned aperture computed tomography (TACT).

Referring again to FIGS. 1 and 2, in block 204, DTS verification image data of target 126 located within or on patient 122 is generated. For example, DTS verification image data generator 124 can be configured to control OBI 102 to acquire a series of cone-beam x-ray projection images of target 126. The images can be acquired using imaging source 112 and imaging panel 116. Verification DTS plans can be reconstructed from the projection data. In one example, a DTS scan can include 81 projections over 40° of gantry rotation and can be acquired in less than 10 seconds. Generally, a DTS scan can include between 40° and 45° of gantry rotation. Other suitable exemplary scan angles are between 10° and 25° and up to 45°.

Figure 4:
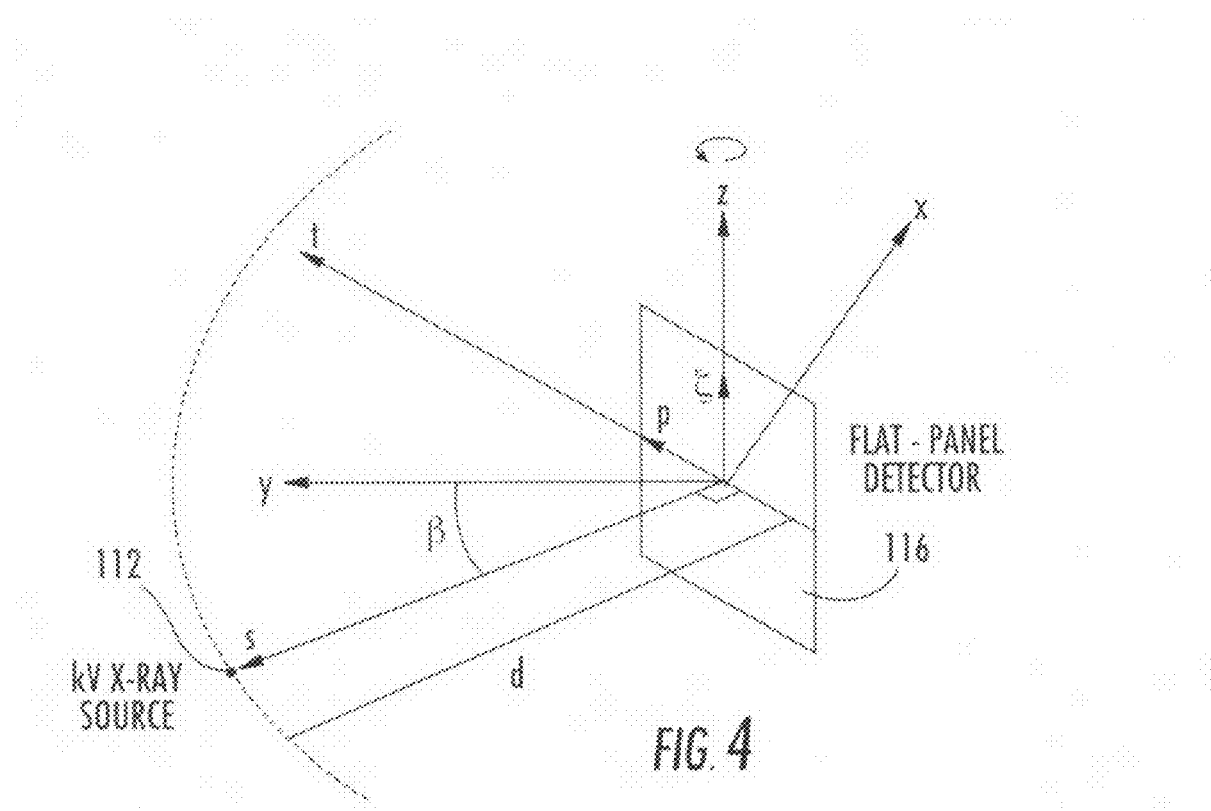
FIG. 4 is a geometric diagram of exemplary positioning of imaging source with respect to an imaging panel.

In one example, DTS verification image data can be generated from subsets of CBCT projection data. FIG. 4 is a geometric diagram illustrating exemplary positioning of imaging source 112 with respect to an imaging panel 116. Referring to FIG. 4, imaging panel (or detector) 116 is positioned at the isocenter for simplification of the reconstruction mathematics. Each projection image is corrected by flood and dark-field images, and the corrected projection data is run through a logarithmic transformation prior to tomographic reconstruction, to remove the exponential function inherent to Beer's law of attenuation. Stacks of DTS slices can be reconstructed using a Feldkamp-type technique as set forth in the following equation.

$$f(x, z | y) = \int_{\beta=\min\beta}^{\max\beta} \frac{d^2}{(d-s)^2} \int_{-\infty}^{\infty} \frac{d}{\sqrt{d^2 + p^2 + \zeta^2}} R(\beta, p, \zeta) h\left(\frac{d \cdot t}{d-s} - p\right) dp \, d\beta$$

In this equation, $f(x,z|y)$ is the reconstructed plane $(x,z)$ through a given depth y, $\beta$ refers to the projection angle, d is the source-to-isocenter distance, $s=-x \sin \beta + y \cos \beta$ is the distance of a voxel from the detector plane, p and $\zeta$ are the detector axes perpendicular and parallel to the axis of rotation, respectively, $R(\beta,p,\zeta)$ is the cone-beam projection, and $h(\cdot)$ denotes a 1-D ramp filter with a Hamming window applied along p with $t=x \cos \beta + y \sin \beta$. Thus, the Feldkamp DTS technique is analogous to Feldkamp CBCT solved only for specified depths y, with a small total scan angle of |βmax−βmin|<<2π.

As set forth above, an advantage of DTS imaging includes rapid image collection with limited source angulation β (or scan angle). For example, source angulation can be between about 40° and 45°. Other suitable exemplary scan angles are between 10° and 25° and up to 45°. Further, for example, a set of about 80 images can be collected in less than 10 seconds. In one example, 81 cone-beam projections images are simulated over 40° of motion about the treatment isocenter (therapy target), with a source-to-isocenter distance (SAD) of 100.0 cm, and an isocenter-to-detector distance (OID) of 50.0 cm.

DTS slice images can be generated from projections obtained with a detector centered relative to an x-ray source. However, in routine CBCT scans of the thorax, abdomen, and pelvis, the detector may be shifted to an off-axis position ("half fan" mode) to obtain a large field-of-view (FOV) CBCT. This mode relies upon a full 360° scan to fill in missing data created by the detector offset. As a result of the detector shift, DTS reconstructions from a small subset of a half-fan CBCT projection data contain only half of the desired FOV.

In one embodiment, large "virtual" forward projections through the large FOV CBCT volume are computed. Next, large FOV DTS slices can be reconstructed from the computed projection images. Alternatively, the large FOV DTS may be generated by carefully merging two half-view DTS images reconstructed using two individual 180° projection data.

Referring again to FIGS. 1 and 2, in block 206, the DTS verification image data is compared with the DTS reference image data of target 126. For example, data comparator 128 can be configured to compare the DTS verification image data with the DTS reference image data of target 126. As a result, DTS verification images can be registered with DTS reference images, which share similar image information, for target verification. Target localization can be performed by comparing landmarks in the DTS reference and verification image data.

In block 208, patient radiotherapy positioning information is determined based on the comparison of the DTS verification and reference image data. For example, radiotherapy positioning module 130 can be configured to determine radiotherapy positioning information for patient 122 based on the comparison of the DTS verification and reference image data. Based on the comparison, patient set-up error for radiotherapy can be determined. Further, the radiotherapy positioning information can be presented to the operator via a display (block 210). A medical practitioner can reposition patient 122 based on the information. The patient can be repositioned and additional comparisons performed until a target is properly localized for radiotherapy.

Figure 5:
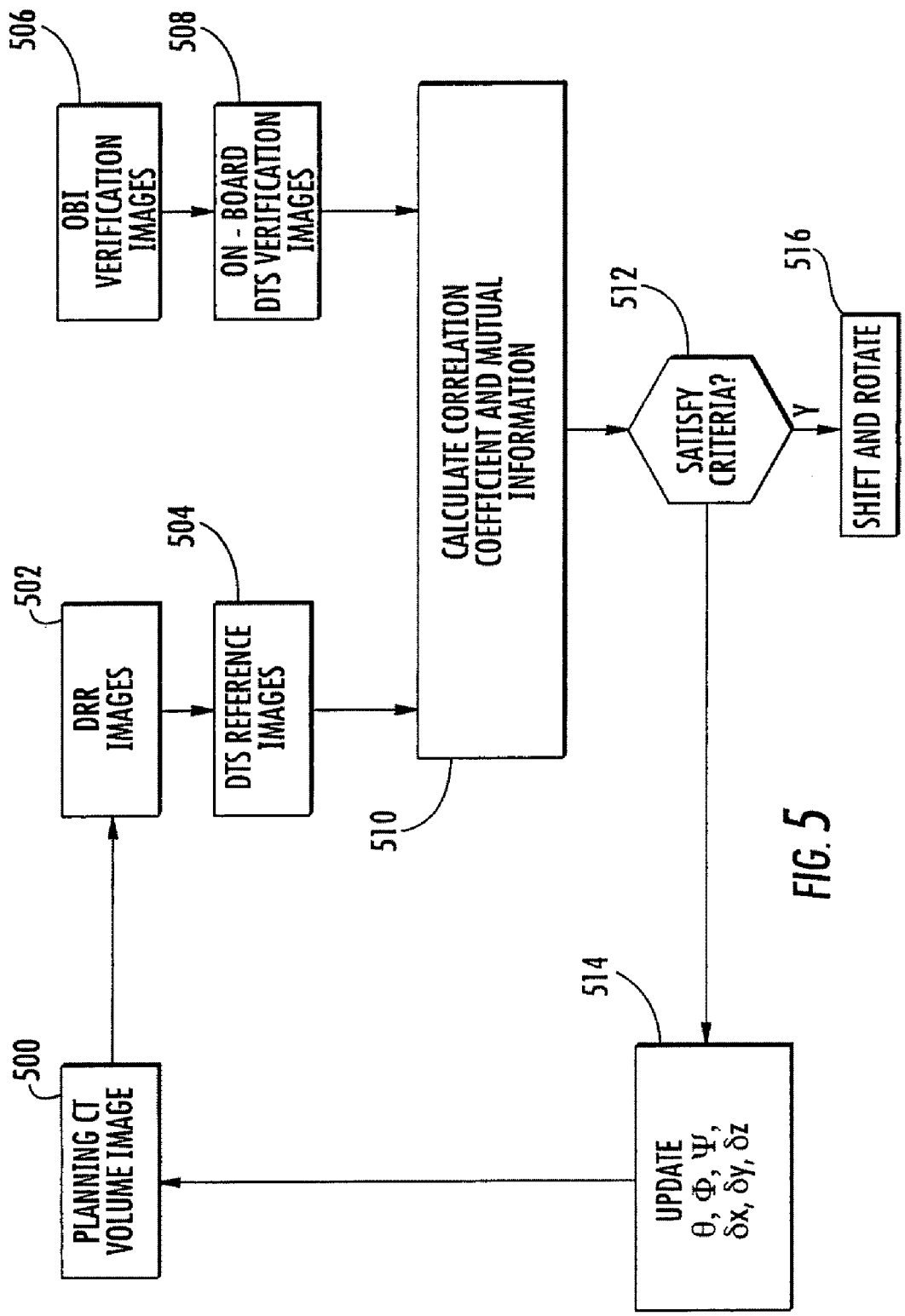
FIG. 5 is a flow chart of an exemplary process for comparing DTS verification and reference image data according to an embodiment of the subject matter described herein.

DTS verification image data of a target can be automatically compared with DTS reference image data of the target in accordance with an embodiment of the subject matter described herein. As stated hereinabove, data comparator 128 can be configured to compare the DTS verification image data with the DTS reference image data of a target. FIG. 5 is a flow chart illustrating an exemplary process for comparing DTS verification and reference image data according to an embodiment of the subject matter described herein. Referring to FIG. 5, a planning CT volume image 500 of a target is used for generating multiple cone-beam DRR images 502. Next, DTS reference images 504 can be generated using a Feldkamp DTS algorithm.

OBI verification images 506 can be obtained using an OBI, such as OBI 102 shown in FIG. 1A. OBI verification images 506 can be used for generating on-board DTS verification images 508. DTS verification image data generator 124 (shown in FIG. 1A) can generate DTS verification image data of a target located within or on a patient.

In block 510, correlation coefficient and mutual information is calculated. In one example, the correlation coefficient and the mutual information are calculated by DTS verification and reference image data comparator 128 shown in FIG. 1A. The correlation coefficient and the mutual information are used to measure image similarity. Correlation measures can be used as initial criteria for updating shift and rotation parameters. The mutual information can be used for fine-tuning.

True correlation coefficient and mutual information can be defined in accordance with the following equations:

$$CorrelationCoefficient(X, Y) = \frac{E(X - E(X))E(X - E(X))}{\sqrt{D(X)}\sqrt{D(Y)}} \text{ and}$$

$$MutualInformation(X, Y) = \sum_{x,y} p(X, Y)\log_2 \frac{p(X, Y)}{p(X)p(Y)},$$

where E(.) is the mathematical expectation, and D(.) is the variance. p(X,Y) is the joint probability density function (PDF) of random variables X and Y, and p(X) and p(Y) are the marginal PDFs. X and Y are grey levels. In the image registration context, X and Y are the normalized one-dimensional vectors with corresponding elements from each image set, and p(X) and p(Y) are the normalized histograms of image X and image Y. p(X,Y) is the normalized joint histogram of them. The similarity measure is defined as either Correlation-Coefficient($S_{CC}$) or MutualInformation($S_{MI}$), shared by on-board and DTS reference volumes:

$$S_{CC}(x) = CorrelationCoefficient(DTS_{reference}(x), DTS_{on-board}) \text{ or}$$

$$S_{MI}(x) = MutualInformation(DTS_{reference}(x), DTS_{on-board})$$

where x=[rx, ry, rz, tx, ty, tz] defines three rotations and three translations from the isocenter CT pose.

The optimization process uses a downhill simplex method, a linear fitting procedure to mathematical functions which may be applied to non-linear problems. The method may only utilize function evaluations, not derivatives. It uses linear adjustment of the parameters until some convergence criterion is met at block 512. The algorithm is given an initial set of vectors in the simplex and proceeds to find the function minimum by a process of reflection expansion and contraction of the simplex (block 514). The algorithm invariably converges to a minimum following a series of contractions so that the final simplex contains very similar vectors in each column. Once it is determined that the criterion is satisfied at block 512, the patient and/or target may be shifted and rotated based on the comparison for correcting patient set-up error.

The subject matter described herein may be implemented using a computer readable medium containing a computer program, executable by a machine, such as a computer. Exemplary computer readable media suitable for implementing the subject matter described herein include chip memory devices, disk memory devices, programmable logic devices, application specific integrated circuits, and downloadable electrical signals. In addition, a computer-readable medium that implements the subject matter described herein may be located on a single device or computing platform or may be distributed across multiple devices or computing platforms.

As used herein, a "computer readable medium" can be any means that can contain, store, communicate, propagate, or transport the computer program for use by or in connection with the instruction execution machine, system, apparatus, or device. The computer readable medium can be, for example, but not limited to, an electronic, magnetic, optical, electromagnetic, infrared, or semiconductor machine, system, apparatus, device, or propagation medium.

More specific examples (a non-exhaustive list) of the computer readable medium can include the following: a wired network connection and associated transmission medium, such as an ETHERNET transmission system, a wireless network connection and associated transmission medium, such as an IEEE 802.11(a), (b), or (g) or a BLUETOOTH transmission system, a wide-area network (WAN), a local-area network (LAN), the Internet, an intranet, a portable computer diskette, a random access memory (RAM), a read only memory (ROM), an erasable programmable read only memory (EPROM or Flash memory), an optical fiber, a portable compact disc (CD), a portable digital video disc (DVD), and the like.

The executable instructions of a computer program for carrying out the methods illustrated in FIGS. 2 and 5 can be embodied in any machine or computer readable medium for use by or in connection with an instruction execution machine, system, apparatus, or device, such as a computer-based or processor-containing machine, system, apparatus, or device, that can read or fetch the instructions from the machine or computer readable medium and execute the instructions.

Experimentation

Experiments were conducted using systems and methods in accordance with the subject matter described herein. For the purpose of comparison, DRR, MV, and kV radiographs of the same anatomic regions were acquired.

FIGS. 6A-6D are DTS reference and verification images of a head-and-neck subject in coronal and sagittal views acquired using systems and methods in accordance with the subject matter described herein. In particular, FIGS. 6A and 6B are DTS reference and verification images, respectively, of the head-and-neck subject in the coronal view. FIGS. 6C and 6D are DTS reference and verification images, respectively, of the head-and-neck subject in the sagittal view.

CT and CBCT images of the head-and-neck subject shown in FIGS. 6A-6D were acquired for the purpose of comparison. FIGS. 7A-7D are planning CT and CBCT images from the head-and-neck subject shown in FIGS. 6A-6D. In particular, FIGS. 7A and 7B are planning CT and CBCT images from the head-and-neck subject in the coronal view. FIGS. 7A and 7B are planning CT and CBCT images of the head-and-neck subject in the sagittal view. In comparison, DTS images in accordance with the subject matter described herein appear to provide equivalent 3-D tissue information as compared with CBCT images. DTS image acquisition in accordance with the subject matter described herein provides the advantage of much less exposure and less risk of geometric collision.

DRR, MV, and kV radiographs of the head-and-neck subject shown in FIGS. 6A-6D were acquired for the purpose of comparison. FIGS. 8A-8E are planning DRR, MV, and kV radiographs of the head-and-neck subject shown in FIGS. 6A-6D. In particular, FIGS. 8A-8C are DRR, MV, and kV radiographs, respectively, from the head-and-neck subject shown in FIGS. 6A-6D in the coronal view. FIGS. 8D and 8E are DRR and MV radiographs, respectively, from the head-and-neck subject shown in FIGS. 6A-6D in the sagittal view.

FIGS. 9A-9D are DTS reference and verification images of a prostate subject in the coronal view acquired using systems and methods in accordance with the subject matter described herein. In particular, FIGS. 9A and 9B are DTS reference and verification images, respectively, of the prostate subject. FIGS. 9C and 9D are DTS reference and verification images, respectively, of the prostate subject.

CT and CBCT images of the head-and-neck subject shown in FIGS. 9A-9D were acquired for the purpose of comparison. FIGS. 10A and 10B are planning CT and CBCT images, respectively, of the prostate subject shown in FIGS. 9A-9D in the coronal view.

DRR, MV, and kV radiographs of the head-and-neck subject shown in FIGS. 9A-9D were acquired for the purpose of comparison. FIGS. 11A-11C are planning DRR, MV, and kV radiographs, respectively, of the prostate subject shown in FIGS. 9A-9D in the coronal view.

In one experiment, the effect of respiratory motion on DTS image quality was investigated. Results of the experiment indicate that breath-hold DTS images acquired in accordance with the subject matter described herein are superior to free-breathing CBCT images. Further, the experiment indicates that DTS images are superior to conventional 2-D localization images and equivalent to CBCT for target localization purposes.

FIGS. 12A and 12B are DTS reference and verification images, respectively, of a breath-hold liver subject acquired using systems and methods in accordance with the subject matter described herein. FIGS. 13A and 13B are planning CT images of the subject shown in FIGS. 12A and 12B in coronal and sagittal views, respectively. FIGS. 14A and 14B are orthogonal kV radiographs of the subject shown in FIGS. 12A and 12B.

In another experiment, CBCT and DTS images were acquired from a thoracic subject for comparison purposes. FIGS. 15A and 15B are CBCT and DTS images, respectively, of the thoracic subject in coronal and sagittal views. The DTS images are acquired using systems and methods according to the subject matter described herein. The experiment demonstrates that the breath-hold DTS images are at least equivalent to CBCT for target localization purposes.

In yet another experiment, breath-hold, free-breathing DTS images and a CBCT image were acquired of a liver subject in accordance with the subject matter described herein. FIGS. 16A and 16B are breath-hold reference and verification DTS images, respectively, of the liver subject in the coronal view.

FIG. 17 is a free-breathing DTS image of the same liver subject in the coronal view. FIG. 18 is a free-breathing CBCT image of the same liver subject in the coronal view. These images provide a comparison of breath-hold and free-breathing images.

In general, a 45° DTS scan can be acquired in less than 10 seconds, making rapid breath-hold DTS a simple technique for acquiring 3-D treatment verification images of abdominal and thoracic sites that are devoid of respiratory motion. FIGS. 19A and 19B are breath-hold reference and verification DTS images, respectively, of a liver subject acquired in accordance with the subject matter described herein. For the purpose of comparison, FIGS. 20A and 20B are breath-hold planning CT and free-breathing on-board CBCT images, respectively, of the same liver subject shown in FIGS. 19A and 19B. Referring to FIG. 20B, the free-breathing CBCT scan renders a surgically implanted surrogate more than 2 cm too superior, while the breath-hold DTS shown in FIGS. 19A and 19B reconstructs the surrogate in its correct location, at full inspiration. This experiment demonstrates that breath-hold DTS provides the best visibility and localization of a target.

The effect of scan angle on DTS image content was examined by computing the mutual information in matching a set of DTS slices and CBCT through the isocenter of a head-and-neck subject. The DTS scan angles of 0°-165° were used in the computations according to the following equation:

$$MI(DTS, CBCT) = \sum_{i,j} P(DTS = i, CBCT = j) \cdot \log_2 \frac{P(DTS = i, CBCT = j)}{P(DTS = i) \cdot P(CBCT = j)},$$

where MI(DTS,CBCT) is the mutual information shared between a DTS slice and the reference CBCT slice, P(DTS=i, CBCT=j) refers to the joint probability distribution of gray-scale values in the two image sets, and P(DTS=i) and P(CBCT=j) are the marginal probability distributions of each image.

Figure 21:
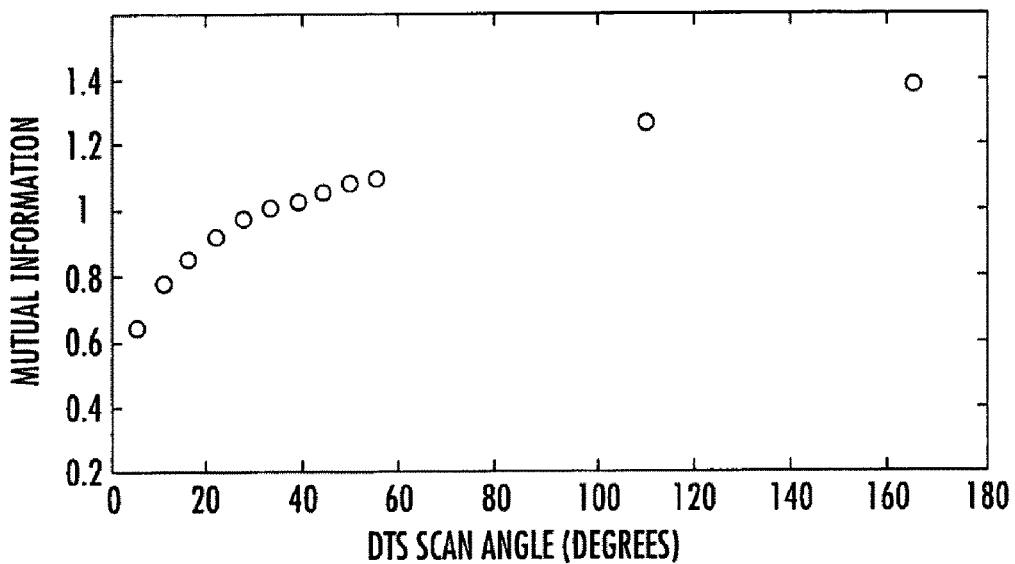
FIG. 21 is a graph of mutual information versus DTS scan angle in a coronal isocenter slice.
Figure 22:
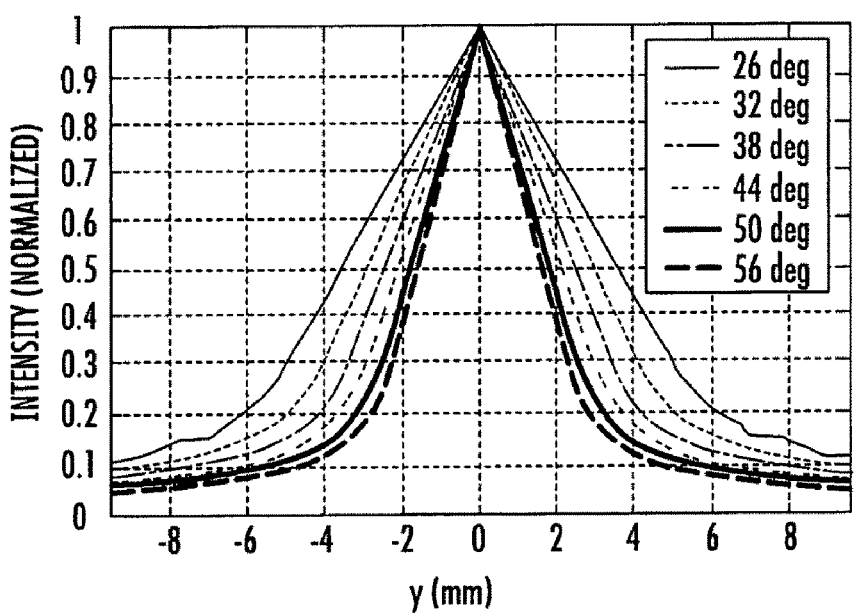
FIG. 22 is a graph of the transfer of information (the point-spread function) in the plane-to-plane dimension (analogous to slice thickness) for various DTS scan angles, reflecting blurring effect of DTS images.

FIG. 21 is a graph illustrating mutual information versus DTS scan angle in a coronal isocenter slice. Referring to FIG. 21, mutual information between DTS and CBCT in the coronal isocenter slice is shown. This data indicates similarity improves with increased DTS scan angle. Minimum mutual information occurs at 0° in the case of a single kV radiograph. FIG. 22 is a graph illustrating the transfer of information (the point-spread function) in the plane-to-plane dimension (analogous to slice thickness) for various DTS scan angles, reflecting blurring effect of DTS images.

As set forth above, a process in accordance with the subject matter described herein can be utilized to compare verification DTS images with reference DTS images. In one experiment, a phantom study was conducted to examine registration accuracy of the process. In the experiment, six non-coplanar BBs were taped onto the phantom and used to determine a true rigid-body registration of reference and verification (or on-board) image data. Reference DTS images were reconstructed from DRRs calculated from a planning CT. On-board DTS images were reconstructed from OBI projection images. Reference DTS volumes were then registered to the corresponding on-board DTS volumes based on measured 3D-3D correlation and mutual information. Correlation measures were the initial criteria used for updating shift and rotation parameters, and mutual information was employed for fine-tuning. An example of this comparison process is described herein with respect to FIG. 5.

Figure 23A:
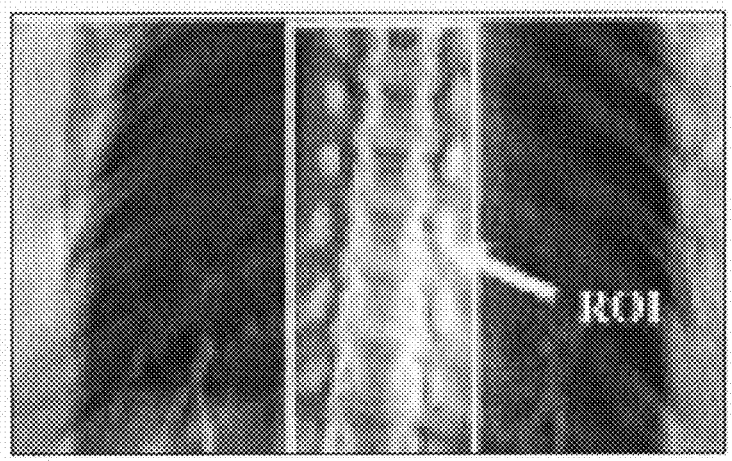
FIGS. 23A and 23B are phantom study images of the chest phantom used for testing the image fusion method.
Figure 23B:
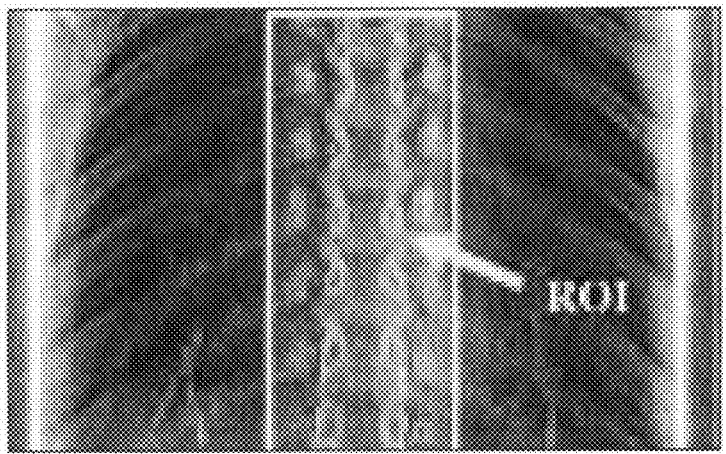

In one evaluation, the comparison process was tested using real reference and on-board DTS data of a chest phantom with known shifts and rotations. FIGS. 23A and 23B are phantom study images of the chest phantom. Evaluation results are provided in Table 1 below.

TABLE 1

| Actual Rotation and Shifts and Error Between Actual Value and Registration | | | | |
|---|---|---|---|---|
| Actual Rotation & Shifts (deg/mm) | Error Between Actual Value and Registration | | | |
| | Rotation (deg) | X (mm) | Y (mm) | Z (mm) |
| −7.0/7.0 | 0.0 | −0.1 | −0.2 | 0.4 |
| −6.0/6.0 | 0.0 | 0.0 | −0.3 | 0.1 |
| −5.0/5.0 | 0.0 | 0.0 | −0.3 | 0.6 |
| −4.0/4.0 | 0.1 | 0.1 | −0.3 | 0.2 |
| −3.0/3.0 | 0.0 | 0.2 | −0.3 | 0.0 |
| −2.0/2.0 | 0.0 | 0.1 | −0.3 | 0.1 |
| −1.0/1.0 | 0.0 | 0.3 | −0.3 | 0.5 |
| 0.0/0.0 | 0.1 | 0.1 | −0.5 | 0.6 |
| 1.0/1.0 | 0.0 | 0.3 | −0.3 | 0.4 |
| 2.0/2.0 | 0.1 | 0.4 | −0.4 | 0.5 |
| 3.0/3.0 | 0.0 | 0.4 | −0.3 | 0.6 |
| 4.0/4.0 | 0.0 | 0.4 | −0.4 | 0.6 |
| 5.0/5.0 | 0.0 | 0.5 | −0.4 | 0.6 |
| 6.0/6.0 | 0.0 | 0.5 | −0.4 | 0.7 |

In all cases shown in Table 1, residual error is less than 1 mm translation, or 0.1° rotation. The results of this experiment show that the resolution of the original planning CT was 0.9 mm in X-axis, 0.9 mm in Y-axis, and 1.0 mm in Z-axis directions. The presence of some systematic errors in the registrations are likely due to imprecise localization of the BBs, resulting from the poor resolution of the planning CT.

Clinical Study for Target Localization Accuracy Using DTS

In this section, data is presented to evaluate the clinical efficacy of 3-D DTS for target localization in radiation therapy under an IRB-approved protocol. The purpose of the study was to determine whether DTS is superior to 2-D-based planar images and comparable to 3-D CBCT.

Patient data was acquired using both 2-D and 3-D techniques on a weekly basis. A total of fourteen (14) target localization procedures from three (3) patients were performed. After the patient was positioned according to the alignment of skin markers with in-room lasers, two orthogonal kV portal images and on-board CBCT scan were acquired. Two subsets of projection data from the CBCT acquisition were extracted to reconstruct DTS images in coronal and sagittal views. The effect of DTS scan angle on localization accuracy was investigated by reconstructing two sets of DTS images with scan angles of 40 degrees (DTS40) and 20 degrees (DTS20), corresponding to 1/9 or 1/18 of the full-rotation CBCT dose, respectively.

The target localization was independently performed using the 2-D radiography, 3-D CBCT, and DTS imaging techniques. To determine the positioning deviation, the on-board 2-D radiographs, CBCT, and DTS images were compared to their corresponding reference images reconstructed from planning CT, respectively. Both bony structures and soft tissues were used as landmarks for patient alignment. The target localization corrections relative to skin markers were recorded for all three techniques.

Comparing 2-D radiography to CBCT, the means and standard deviations for localization differences were 0.2±0.2 cm, 0.3±0.3 cm, and 0.3±0.1 cm in the AP, SI, and lateral directions, respectively. The vector difference was 0.49±0.25 cm. Comparing 2-D radiography and DTS, the mean and standard deviations for localization differences were 0.3±0.3 cm (AP), 0.3±0.3 cm (SI), and 0.2±0.1 cm (lateral). The vector difference was 0.51±0.25 cm. Comparing DTS to CBCT, the means and standard deviations for localization differences were 0.1±0.1 cm in all directions, indicating that the two techniques are comparable with the limitation of imaging resolution. The statistical correlation coefficient between the DTS and 2-D localization was 0.49, while for DTS and CBCT localization the statistical correlation coefficient was 0.86. Localization accuracy using DTS images reconstructed with 40 and 20 degrees of scan angle yielded very similar results (correlation coefficient=0.92). This suggests that with only 20 degrees of gantry rotation and 1/18 of CBCT dose, DTS may be effective for daily 3-D target localization.

Based on these experimental results, it is apparent that the systems and methods described herein provide an attractive intermediary between the anatomic visibility provided by 2-D radiographic localization techniques, and the long acquisition time/high patient dose of full 3-D CBCT, and is therefore likely to be a good alternative for daily radiation therapy patient positioning. Further, the subject matter described herein provides techniques of implementing online DTS for radiation therapy target localization, complete with the creation of matching DTS reference and verification image data. A full DTS reference and verification localization technique has been described herein for external-beam radiation therapy applications.

Further, the systems and methods described herein are advantageous because the DTS image data can be generated from planning CT data. Therefore, for example, the equipment for acquiring the DTS image data may be standard hardware. For example, the DTS verification image data can be acquired with a kV x-ray tube and flat-panel detector, mounted on a treatment gantry. Such equipment is standard for on-board CBCT acquisition systems, whose use is rapidly expanding. As a result, the DTS techniques described herein, such as target localization, can be implemented using currently available commercial radiation therapy equipment.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for localizing a target for radiotherapy based on digital tomosynthesis (DTS), the method comprising:
   (a) generating DTS verification image data of a target located within or on a patient;
   (b) comparing the DTS verification image data with DTS reference image data of the target; and
   (c) determining radiotherapy positioning information based on the comparison of the DTS verification and reference image data.

2. The method of claim 1 wherein generating DTS verification image data comprises acquiring cone-beam projection images of the target.

3. The method of claim 2 wherein acquiring cone-beam projection images comprises acquiring the cone-beam projection images at scan angles between about 10° and 45°.

4. The method of claim 3 wherein acquiring the cone-beam projection images includes acquiring the cone-beam projection images in less than 10 seconds with or without the use of any respiratory motion management devices.

5. The method of claim 1 wherein determining radiotherapy positioning information comprises comparing landmarks in the DTS reference and verification image data.

6. The method of claim 1 wherein comparing the DTS verification image data with the DTS reference image data comprises calculating a correlation coefficient based on the DTS reference and verification image data.

7. The method of claim 1 wherein comparing the DTS verification image data with the DTS reference image data comprises calculating mutual information based on the DTS reference and verification image data.

8. The method of claim 1 comprising generating the DTS reference image data based on CT image volume data of the target.

9. The method of claim 8 wherein generating the DTS reference image data comprises reconstructing the DTS reference image data from simulated cone-beam projections through the CT image volume data.

10. The method of claim 9 wherein reconstructing the DTS reference image data comprises computing the simulated cone-beam projections by integrating attenuation values along ray-paths extending from a predetermined location of an x-ray source to a predetermined location of an x-ray detector pixel.

11. The method of claim 10 comprising selecting the predetermined x-ray source and detector locations to match actual source and detector pixel locations.

12. The method of claim 8 wherein the CT image volume data includes CT slices stacked together to form a 3-D volume of the target.

13. The method of claim 1 comprising generating the DTS reference image data of the target.

14. The method of claim 13 wherein generating the DTS reference image data of the target comprises generating cone-beam computed tomography (CBCT) image data of the target.

15. The method of claim 13 wherein the DTS reference image data of the target is based on the CBCT image data of the target.

16. The method of claim 1 comprising generating the DTS reference image data of the target directly from CBCT image data of the target.

17. The method of claim 1 comprising generating the DTS reference image data of the target based on simulator projection image data of the target.

18. The method of claim 17 comprising acquiring the simulator projection image data of the target using an x-ray tube and a flat panel detector.

19. The method of claim 17 comprising acquiring the simulator projection image data of the target using an x-ray tube and an image intensifier.

20. The method of claim 1 comprising generating the DTS reference image data of the target based on a mobile c-arm x-ray unit projection image data of the target.

21. The method of claim 20 comprising acquiring the c-arm x-ray unit projection image data of the target using an x-ray tube and a flat panel detector.

22. The method of claim 20 comprising acquiring the c-arm x-ray unit projection image data of the target using an x-ray tube and an image intensifier.

23. A system for localizing a target for radiotherapy based on digital tomosynthesis (DTS), the system comprising:
   (a) a DTS verification image data generator configured to generate DTS verification image data of a target located within or on a patient;
   (b) a DTS verification and reference image comparator configured to compare the DTS verification image data with DTS reference image data of the target; and
   (c) a radiotherapy positioning module configured to determine radiotherapy positioning information based on the comparison of the DTS verification and reference image data.

24. The system of claim 23 wherein the DTS verification image generator is configured to acquire cone-beam projection images of the target.

25. The system of claim 24 wherein the DTS verification image generator is configured to acquire the cone-beam projection images at scan angles between about 10° and 45°.

26. The system of claim 25 wherein the DTS verification image generator is configured to acquire the cone-beam projection images in less than 10 seconds.

27. The system of claim 23 wherein the radiotherapy positioning module is configured to compare landmarks in the DTS reference and verification image data.

28. The system of claim 23 wherein the radiotherapy positioning module is configured to calculate a correlation coefficient based on the DTS reference and verification image data.

29. The system of claim 23 wherein the radiotherapy positioning module is configured to calculate mutual information based on the DTS reference and verification image data.

30. The system of claim 23 comprising a DTS reference image data generator configured to generate the DTS reference image data based on CT image volume data of the target.

31. The system of claim 30 wherein the DTS reference image data generator configured to reconstruct the DTS reference image data from simulated cone-beam projections through the CT image volume data.

32. The system of claim 30 wherein the DTS reference image data generator configured to compute the simulated cone-beam projections by integrating attenuation values along ray-paths extending from a predetermined location of an x-ray source to a predetermined location of an x-ray detector pixel.

33. The system of claim 32 wherein the DTS verification and reference image comparator is configured to select the predetermined x-ray source and detector locations to match actual source and detector pixel locations.

34. The system of claim 30 wherein the CT image volume data includes CT slices stacked together to form a 3-D volume of the target.

35. The system of claim 23 comprising a DTS reference image data generator configured to generate the DTS reference image data of the target.

36. The system of claim 35 wherein the DTS reference image data generator is configured to generate cone-beam computed tomography (CBCT) image data of the target.

37. The system of claim 35 wherein the DTS reference image data of the target is based on the CBCT image data of the target.

38. The system of claim 23 comprising a DTS reference image data generator configured to generate the DTS reference image data of the target directly from CBCT image data of the target.

39. The system of claim 23 comprising a DTS reference image data generator configured to generate the DTS reference image data of the target based on simulator projection image data of the target.

40. The system of claim 39 comprising an x-ray tube and a flat panel detector configured to acquire the simulator projection image data of the target.

41. The system of claim 39 comprising an x-ray tube and an image intensifier configured to acquire the simulator projection image data of the target.

42. The system of claim 23 comprising a DTS reference image data generator configured to generate the DTS reference image data of the target based on a mobile c-arm x-ray unit projection image data of the target.

43. The system of claim 42 comprising an x-ray tube and a flat panel detector configured to acquire the c-arm x-ray unit projection image data of the target.

44. The system of claim 42 comprising an x-ray tube and an image intensifier configured to acquire the c-arm x-ray unit projection image data of the target.

* * * * *